United States Patent [19]
Obeng

[11] Patent Number: 5,670,376
[45] Date of Patent: Sep. 23, 1997

[54] METHODOLOGY FOR MONITORING SOLVENT QUALITY

[75] Inventor: Yaw Samuel Obeng, Orlando, Fla.

[73] Assignee: Lucent Technologies Inc., Murray Hill, N.J.

[21] Appl. No.: 355,787

[22] Filed: Dec. 14, 1994

[51] Int. Cl.[6] ............................................. G01N 35/00
[52] U.S. Cl. ........................................... 436/55; 134/18
[58] Field of Search ................................. 436/55; 134/1, 134/1.3, 18; 156/625, 654, 657; 252/162

[56] References Cited

U.S. PATENT DOCUMENTS

| | | | |
|---|---|---|---|
| 4,682,113 | 7/1987 | Barben, II | 324/441 |
| 4,795,497 | 1/1989 | McConnell et al. | 134/18 |
| 4,824,763 | 4/1989 | Lee | 252/153 |
| 4,857,750 | 8/1989 | Millis et al. | 250/573 |
| 5,091,103 | 2/1992 | Dean et al. | 252/162 |
| 5,225,048 | 7/1993 | Yuan | 203/1 |
| 5,364,510 | 11/1994 | Carpio | 134/2 |

FOREIGN PATENT DOCUMENTS

A-28 05 161  8/1978  Germany.

OTHER PUBLICATIONS

Patent Abstract of JP-A-62 091105 (Katsura Shigeo) Apr. 1993.

*Primary Examiner*—Jeffrey Snay
*Assistant Examiner*—Alexander Markoff
*Attorney, Agent, or Firm*—J. T. Rehberg

[57] ABSTRACT

The quality of solvents used in semiconductor manufacturing for removing photoresist or post halogen etch cleanup is monitored by measuring the conductivity of the solvents.

5 Claims, 2 Drawing Sheets

METHODOLOGY FOR MONITORING SOLVENT QUALITY

TECHNICAL FIELD

This invention relates to methods and apparatus for integrated circuits processing.

BACKGROUND OF THE INVENTION

Organic solvent blends with various active chemical bases are used in the microelectronics industry to remove photoresist and photoresist derivatives during integrated circuit fabrication. These solvents employ a variety of physical and chemical mechanisms, e.g., penetration, swelling, and dissolution, for photo resist removal. A wide variety of solvent blends utilizing different chemical bases are marketed by different vendors. A few examples of solvent blends together with their principle chemical base and commercial vendors are compiled in Table 1.

TABLE 1

| | Solvent Base | Chemical Base | Vendor |
|---|---|---|---|
| 1 | NMP | Aminoethyl Piperadine | Allied Chemical |
| 2 | NMP/DMF/Sulfolane | — | Shipley |
| 3 | NMP | Isopropyl Amine | J. T. Baker |
| 4 | NMP | Amine | Olin Hunt |
| 5 | NMP | Hydroxylethyl Morpholine | Mac Dermid |
| 6 | DMSO | Amino Alcohol | Asahi Chemicals |
| 7 | DMSO | Amino Alcohol | Tokyo Ohka |
| 8 | NMP/DMF | Dietlylenetriamine | EKC Technology |
| 9 | DMAC | Diethnolamine | AKT, Inc. |
| 10 | DMAC | Amine | Hitachi |
| 11 | DMF | Amino Alcohol | Asahi Kasei |
| 12 | NMP or DMF | Ammonium Salt | Hoechst Japan |

These solvents are predominately primary and secondary amines and they tend to be very susceptible to hydrolysis from moisture, as illustrated in Equation 1.

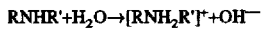

$$RNHR' + H_2O \rightarrow [RNH_2R']^+ + OH^- \quad (1)$$

Those concerned with the development of integrated circuits have continuously sought methods and apparatus for the effective monitoring of organic solvent performance and organic material removal in microelectronic manufacturing.

SUMMARY OF THE INVENTION

Improved microelectronic fabrication is accomplished by the present invention which illustratively includes exposing a substrate to an organic solvent. The conductivity of the solvent is measured and when the conductivity reaches a predetermined value, the exposure of the substrate to the solvent is terminated.

DETAILED DESCRIPTION

The reactive Hydroxyl ($OH^-$) ions in equation (1) tend to attack, corrode or dissolve metals and glass films. Consequently, the effectiveness of a solvent which has been exposed to or absorbed too much moisture is considerably reduced. Applicants have discovered that it is extremely beneficial to continuously monitor the concentration of water in organic solvents utilized during integrated circuit processing. Dynamic monitoring of the concentration of water in various organic solvent blends used in integrated circuit fabrication utilizing a conductivity bridge has been shown to produce improved integrated circuits.

Pure organic solvents have high electrical resistances because they do not contain appreciable concentrations of charge carriers. However, the resistances decreases and the conductivity increases, when many organic solvents are mixed with water. For solvents utilized currently as photoresist strippers, the reaction indicated above in Equation 1 occurs in the present of water to produce $OH^-$ ions which are charge carders.

Illustratively, a conductivity sensor (e.g. a sensor of the types manufactured by Great Lakes Instrument, Milwaukee, Wis.) may be plumbed/introduced into either solvent tank or solvent flow stream. The conductivity probe may be connected to a computer. The computer is programmed to measure and save the value of the solvent conductivity at the beginning of processing a batch of wafers. Alarm flags may be set and interlocked with wafer handling apparatus so that the equipment will shutdown if a critical conductivity value is exceeded.

Figure 1:
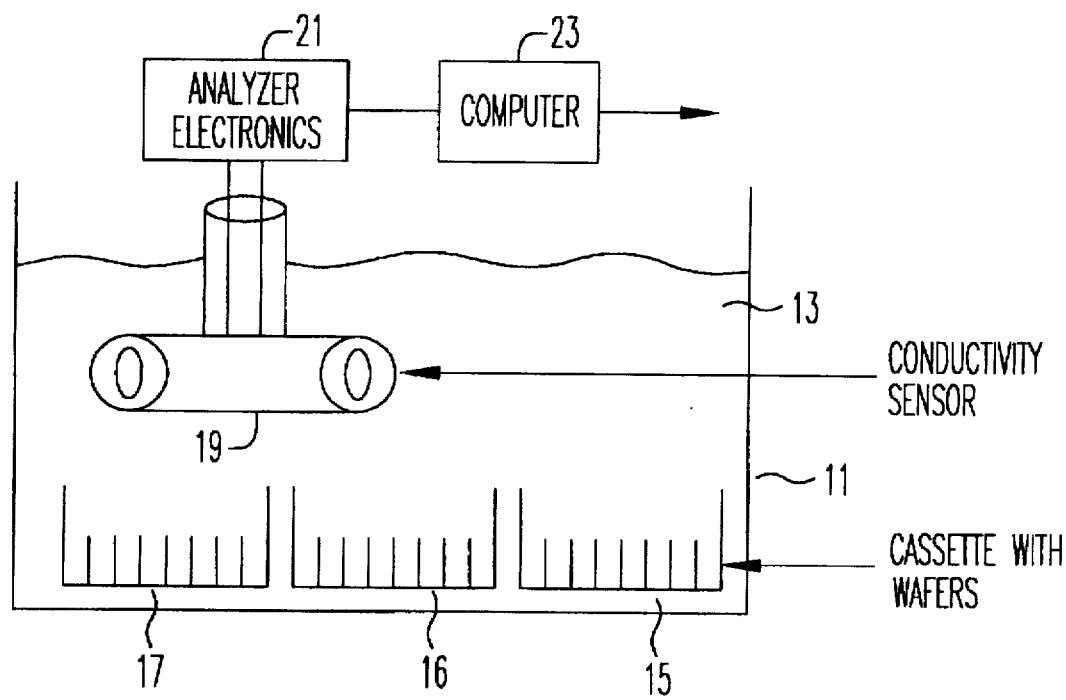
FIGS. 1–3 are diagrams showing illustrative embodiments of the present invention.

An illustrative embodiment of the invention is depicted in FIG. 1. Reference numeral 11 denotes a tank which contains solvent 13. Wafer cassettes 15, 16, and 17 are immersed in tank 11. Conductivity sensor 19 is connected to conductivity analyzer electronics 21. Analyzer electronics are connected to computer 23. In one embodiment, computer 23 may be pre-programmed with a upper conductivity limit. Should the conductivity of solvent 13 exceed the pre-programmed limit, an alarm will be tripped and either cassettes 15, 16, and 17 will be removed from the solvent or no additional cassettes will be admitted to solvent tank 11 until the solvent bath is changed or modified in a mannered to reduce its conductivity.

Figure 2:
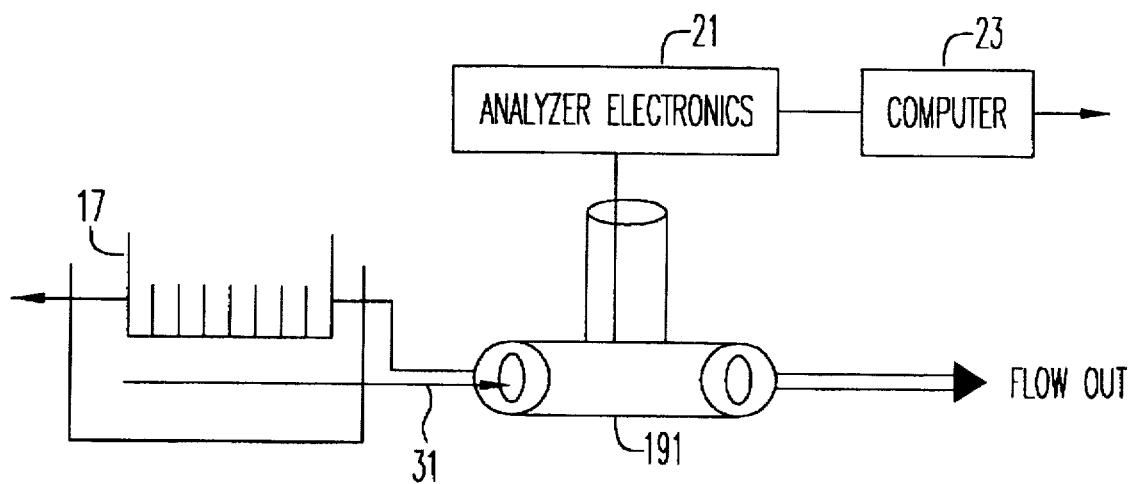

In another embodiment shown in FIG. 2, a sensor 191 may be utilized to monitor the conductivity of a solvent flow stream 31 which bathes wafers 17. The conductivity may be analyzed by analyzer electronics 21 and the output of analyzer electronics 21 provided to computer 23 for appropriate comparison with predetermined values.

Figure 3:
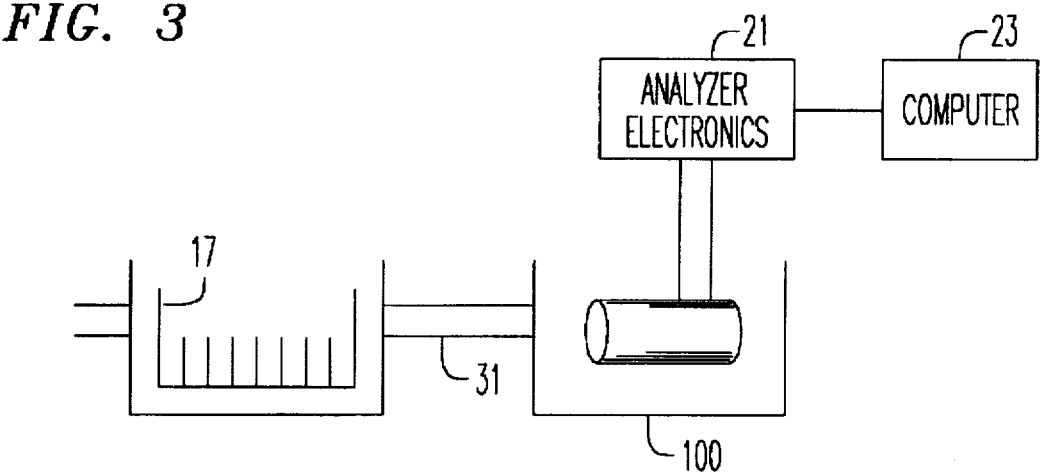
Figure 4:
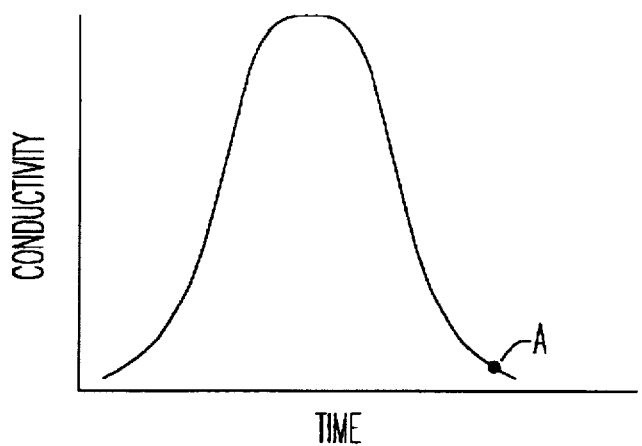
FIGS. 4–5 are graphs useful in understanding illustrative embodiments of the present invention.
Figure 5:
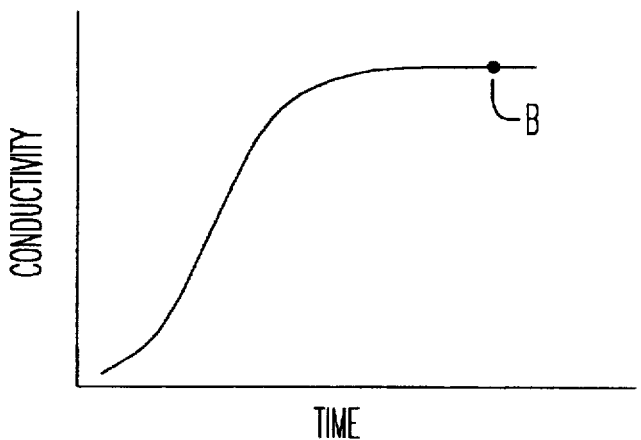

For example, in the cleaning of layers containing charged chemical species (e.g., during post halogen-based reactive ion etch cleanup such as in the etching of aluminum alloys) the conductivity of the solvent will increase as the concentration of charged species enter the fluid stream. FIG. 4 shows a graph of the conductivity of fluid stream 31 as a function of time. When an appropriate end point is reached at point A, the clean-up may be terminated. Alternatively, the apparatus of FIG. 3 may be used. Flow stream may be collected in tank 100 and the conductivity of the fluid in the tank monitored by analyzer 21 and computer 23. FIG. 5 is a graph showing the conductivity of the fluid in tank 100 as a function of time. The "end point" of the cleaning process will coincide with a plateau in the conductivity vs. time curves such as at point B of FIG. 5. Thus, by continuously monitoring the conductivity of the stream 31 in FIG. 2 and 3 containing the charged species, one may be assured that etched aluminum runners are acceptably halogen-free after patterning.

I claim:

1. A method of integrated circuit fabrication comprising:
   exposing a substrate to an organic solvent capable of carrying charged chemical species;

measuring a conductivity of said organic solvent; and terminating said exposure of said substrate to said organic solvent when said conductivity reaches a predetermined value.

2. The method of claim 1 in which said substrate is exposed to said organic solvent by immersing said substrate in a bath of said organic solvent and in which said exposure is terminated by removing said substrate from said bath.

3. The method of claim 1 in which said substrate is exposed to said organic solvent by placing said substrate in a flowing stream of said organic solvent and in which said exposure is terminated by removing said substrate from said flowing stream.

4. The method of claim 2 in which a photoresist material overlies said substrate prior to immersion in said organic solvent and in which said organic solvent removes some of said photoresist material.

5. The method of claim 3 in which said substrate subjected to a process which leaves charged chemical species upon said substrate prior to placement of said substrate in said flowing stream, and in which after immersion in said flowing stream, said flowing stream removes said charged chemical species, and in which said substrate is removed from said flowing stream when said conductivity reaches a predetermined value.

* * * * *